United States Patent
Lubold et al.

(10) Patent No.: US 12,367,876 B2
(45) Date of Patent: *Jul. 22, 2025

(54) SYSTEM AND METHOD FOR REAL-TIME FEEDBACK OF REMOTE COLLABORATIVE COMMUNICATION

(71) Applicant: HONEYWELL INTERNATIONAL INC., Charlotte, NC (US)

(72) Inventors: Nichola Lubold, Phoenix, AZ (US); Tor Finseth, Plymouth, MN (US)

(73) Assignee: HONEYWELL INTERNATIONAL, INC., Charlotte, NC (US)

( * ) Notice: Subject to any disclaimer, the term of this patent is extended or adjusted under 35 U.S.C. 154(b) by 256 days.

This patent is subject to a terminal disclaimer.

(21) Appl. No.: 18/065,248

(22) Filed: Dec. 13, 2022

(65) Prior Publication Data

US 2024/0194196 A1 Jun. 13, 2024

(51) Int. Cl.
*G10L 15/22* (2006.01)
*G10L 17/26* (2013.01)

(52) U.S. Cl.
CPC .............. *G10L 15/22* (2013.01); *G10L 17/26* (2013.01); *G10L 2015/227* (2013.01)

(58) Field of Classification Search
CPC ... G10L 15/22; G10L 17/26; G10L 2015/227; G10L 25/30; G10L 25/66; G10L 25/63; A61B 5/4836; A61B 5/165; A61B 5/4803; A61B 5/7267
USPC ........................................................ 704/275
See application file for complete search history.

(56) References Cited

U.S. PATENT DOCUMENTS

| | | | |
|---|---|---|---|
| 8,062,129 B2 | 11/2011 | Pope et al. | |
| 8,160,210 B2 | 4/2012 | Hause et al. | |
| 9,953,650 B1 | 4/2018 | Falevsky | |
| 10,944,708 B2 | 3/2021 | Anderson et al. | |
| 11,633,103 B1 * | 4/2023 | Nudd | G06F 17/18 704/9 |
| 11,727,954 B2 * | 8/2023 | Shallom | G10L 15/30 704/206 |
| 11,978,445 B1 * | 5/2024 | Bueche | G06F 40/35 |
| 12,057,128 B1 * | 8/2024 | Jayapalan | H04L 9/3231 |
| 2008/0045805 A1 * | 2/2008 | Sarel | A61B 5/164 600/300 |
| 2008/0270123 A1 * | 10/2008 | Levanon | G10L 17/26 704/E11.002 |

(Continued)

OTHER PUBLICATIONS

Pérez, A., Carreiras, M. & Duñabeitia, J.A. Brain-to-brain entrainment: EEG interbrain synchronization while speaking and listening. Sci Rep 7, 4190 (Jun. 23, 2017). (Year: 2017).*

(Continued)

*Primary Examiner* — Thuykhanh Le
(74) *Attorney, Agent, or Firm* — Lorenz & Kopf LLP (57) ABSTRACT

A system and method for providing real-time feedback of remote collaborative communication between users includes extracting speech-related features and physiological features from at least one of the users and using these features to determine a stress state of at least one user. In response to the determined stress state audio signals may be processed to manipulate one or more vocal features of the speech supplied from another user, and/or at least one device may supply feedback to another user that provides suggestions as to how to manipulate or more of their vocal features.

10 Claims, 7 Drawing Sheets

(56) References Cited

U.S. PATENT DOCUMENTS

| | | | |
|---|---|---|---|
| 2011/0144457 A1* | 6/2011 | Coulon | G16Z 99/00 |
| | | | 600/301 |
| 2014/0140497 A1* | 5/2014 | Ripa | H04M 3/5175 |
| | | | 379/265.06 |
| 2014/0278745 A1* | 9/2014 | Herring | G06Q 30/0201 |
| | | | 705/7.29 |
| 2015/0310865 A1 | 10/2015 | Fay et al. | |
| 2016/0111111 A1 | 4/2016 | Levitt | |
| 2017/0322679 A1 | 11/2017 | Gordon | |
| 2018/0133431 A1 | 5/2018 | Malchano et al. | |
| 2018/0240108 A1* | 8/2018 | Boss | G06Q 40/02 |
| 2019/0200888 A1 | 7/2019 | Poltorak | |
| 2019/0311610 A1* | 10/2019 | Jessop | H04Q 9/00 |
| 2019/0357831 A1 | 11/2019 | Avegliano et al. | |
| 2020/0286480 A1 | 9/2020 | Singh et al. | |
| 2021/0023332 A1 | 1/2021 | Auger et al. | |
| 2021/0076002 A1 | 3/2021 | Peters et al. | |
| 2021/0110844 A1 | 4/2021 | Miyake et al. | |
| 2021/0287664 A1* | 9/2021 | Bart | G10L 15/144 |
| 2021/0312923 A1 | 10/2021 | Gaur et al. | |
| 2022/0044683 A1 | 2/2022 | Lubold et al. | |
| 2022/0301563 A1* | 9/2022 | Chang | G10L 15/24 |
| 2023/0069102 A1* | 3/2023 | Jaiswal | H04M 1/575 |
| 2023/0080660 A1* | 3/2023 | Miletic | G10L 15/063 |
| | | | 382/103 |
| 2023/0095526 A1* | 3/2023 | Chen | G10L 25/21 |
| | | | 704/243 |
| 2023/0237242 A1* | 7/2023 | Seroussi | G06F 40/232 |
| | | | 715/200 |
| 2023/0317046 A1* | 10/2023 | Shiao | G10K 11/1783 |
| | | | 700/94 |
| 2023/0352005 A1* | 11/2023 | Akahori | G10L 25/63 |
| 2023/0410801 A1* | 12/2023 | Mishra | G10L 15/22 |
| 2024/0005085 A1* | 1/2024 | Kukde | G10L 25/78 |
| 2024/0096329 A1* | 3/2024 | Wang | G10L 25/63 |
| 2024/0144955 A1* | 5/2024 | Jung | G10L 25/63 |
| 2024/0161373 A1* | 5/2024 | Ray | G06T 13/40 |
| 2024/0164672 A1* | 5/2024 | Pasley | G06F 3/015 |
| 2024/0177711 A1* | 5/2024 | Nelson | G06Q 30/015 |
| 2024/0226477 A1* | 7/2024 | Lyon | A61B 5/4818 |
| 2024/0354389 A1* | 10/2024 | Okada | G06F 21/32 |
| 2025/0041595 A1* | 2/2025 | Baker, Jr. | A61N 1/36003 |
| 2025/0073470 A1* | 3/2025 | Moffitt | A61N 1/025 |

OTHER PUBLICATIONS

Peérez, A., Carreiras, M. & Duñabeitia, J.A. Brain-to-brain entrainment: EEG interbrain synchronization while speaking and listening. Sci Rep 7, 4190 (Jun. 23, 2017). (Year: 2017).*

Lee, Chi-Chun, et al. "Computing vocal entrainment: A signal-derived PCA-based quantification scheme with application to affect analysis in married couple interactions." Computer Speech & Language 28.2 (Nov. 27, 2014): 518-539. (Year: 2014).*

Aftanas, L.I., "Human Anterior and Frontal Midline Theta and Lower Alpha Reflect emotionally Positive State and Internalized Attention: High-resolution EEG Investigation of Meditation," Neuroscience Letters 310, Jul. 12, 2001, 57-60.

L. Alem, F. Tecchia, and W. Huang, "HandsOnVideo: Towards a Gesture based Mobile AR System for Remote Collaboration," in Recent Trends of Mobile Collaborative Augmented Reality Systems, Springer New York, 2011, pp. 135-148.

S. D. ' Angelo and D. Gergle, "An Eye For Design: Gaze Visualizations for Remote Collaborative Work," Apr. 21, 2018.

E. Bartoli, L. Maffongelli, C. Campus, and A. D'Ausilio, "Beta Rhythm Modulation by Speech Sounds: Somatotopic Mapping in Somatosensory Cortex," Scientific Reports, vol. 6, Aug. 2016.

P. Boersma, "Praat, A System for Doing Phonetics by Computer," Glot International, vol. 5, Dec. 2001.

S. Borrie, N. Lubold, and H. Pon-Barry, "Disordered Speech Disrupts Conversational Entrainment: A Study of Acoustic-Prosodic Entrainment and Communicative Success in Populations with Communication Challenges.," Frontiers in Psychology, vol. 6, Aug. 2015, p. 1187, 2015.

K. A. Correa, B. T. Stone, M. Stikic, R. R. Johnson, and C. Berka, "Characterizing Donation Behavior from Psychophysiological Indices of Narrative Experience," Frontiers in Neuroscience, vol. 9, Aug. 2015.

Y. Dich, J. Reilly, and B. Schneider, "Using Physiological Synchrony as an Indicator of Collaboration Quality, Task Performance and Learning," in Lecture Notes in Computer Science (including subseries Lecture Notes in Artificial Intelligence and Lecture Notes in Bioinformatics), 2018, vol. 10947 LNAI, pp. 98-110.

G. Dumas, J. Nadel, R. Soussignan, J. Martinerie, and L. Garnero, "Inter-brain Synchronization During Social Interaction," PLoS One, vol. 5, No. 8, Aug. 2010.

F. Eyben, M. Wollmer, and B. Schuller, "openSMILE—The Munich Versatile and Fast Open-Source Audio Feature Extractor Categories and Subject Descriptors," Proceedings of the 18th ACM international conference on Multimedia, Oct. 2010, pp. 1459-1462.

G. Gweon, M. Jain, J. McDonough, B. Raj, and C. P. Rose, "Predicting Idea Co-Construction in Speech Data Using Insights from Sociolinguistics," 10th Int. Conf. Learn. Sci. Futur. Learn. ICLS 2012—Proc., vol. 1, pp. 435-442, 2012.

K. Inanaga, "Frontal Midline Theta Rhythm and Mental Activity," Psychiatry and Clinical Neurosciences, vol. 52, No. 6, pp. 555-566, Jul. 1998.

S. Järvelá et al., "Enhancing Socially Shared Regulation in Collaborative Learning Groups: Designing for CSCL Regulation Tools," Education Tech Research Dev, vol. 63, pp. 125-142, Oct. 2014.

W. Klimesch, P. Sauseng, and S. Hanslmayr, "EEG Alpha Oscillations: The Inhibition-timing Hypothesis," Brain Research Reviews 53, Jun. 2006.

N. Lubold and H. Pon-Barry, "Acoustic-Prosodic Entrainment and Rapport in Collaborative Learning Dialogues Categories and Subject Descriptors," Proc. 2014 ACM Work. Multimodal Learn. Anal. Work. Gd. Chall., Nov. 2014.

H. Lubold, Nichola; Pon-barry, "A Comparison of Acoustic-Prosodic Entrainment in Remote and Face-to-Face Collaborative Learning Dialogues," pp. 288-293, Nov. 2014.

J. S. P. Macdonald, S. Mathan, and N. Yeung, "Trial-by-trial Variations in Subjective Attentional State are Reflected in Ongoing Prestimulus EEG Alpha Oscillations," Frontiers in Psychology, vol. 2, May 2011, pp. 1-16.

E. Montague, J. Xu, and E. Chiou, "Shared Experiences of Technology and Trust: An Experimental Study of Physiological Compliance Between Active and Passive Users in Technology-Mediated Collaborative Encounters," IEEE Transactions on HUMAN-MACHINE System, vol. 44, No. 5, Oct. 2014.

M. Naeem, G. Prasad, D. R. Watson, and J. A. Kelso, "Electrophysiological Signatures of Intentional Social Coordination in the 10-12 Hz range," NeuroImage, vol. 59, pp. 1795-1803, Aug. 2011.

K. G. Niederhoffer and J. W. Pennebaker, "Linguistic Style Matching in Social Interaction," Journal of Language Social Psychology, vol. 21, No. 4, pp. 337-360, Dec. 2002.

L. M. Oberman, J. A. Pineda, and V. S. Ramachandran, "The Human Mirror Neuron System: A Link Between Action Observation and Social Skills," Social Cognitive Affect. Neuroscience, vol. 2, No. 1, pp. 62-66, Apr. 2006.

M. Otsuki, K. Maruyama, H. Kuzuoka, and Y. Suzuki, "Effects of Enhanced Gaze Presentation on Gaze Leading in Remote Collaborative Physical Tasks," Apr. 2018.

A. Perez, M. Carreiras, and J. Dunabeitia, "Brain-to-Brain Entrainment: EEG Interbrain Synchronization While Speaking and Listening," Scientific Reports, vol. 7, No. 1, Jun. 2017.

Pickering, MJ & Garrod, S 2004, 'The interactive-alignment model: Developments and refinements—Response' Behavioral and Brain Sciences, vol. 27, No. 2, pp. 212-225., 10.1017/S0140525X04450055.

H. J. Pijeira-Diaz, H. Drachsler, Sanna Jarvela, and Paul A. Kirschner, "Investigating Collaborative Learning Success with Physiological Coupling Indices Based on Electrodermal Activity," Proceedings of the Sixth International Conference on Learning Analytics & Knowledge, 2016.

W. J. Ray and H. W. Cole, "EEG Alpha Activity Reflects Emotional and Cognitive Processes," Science, vol. 228, pp. 750-752, Jun. 1985.

(56) References Cited

OTHER PUBLICATIONS

F. Singh, J. Pineda, and K. S. Cadenhead, "Association of Impaired EEG Mu Wave Suppression, Negative Symptoms and Social Functioning in Biological Motion Processing in First Episode of Psychosis," Schizophr. Res., vol. 130, No. 1, pp. 182-186, Aug. 2011.
S. Weiss and H. M. Mueller, "'Too Many Betas Do Not Spoil the Broth': The Role of Beta Brain Oscillations in Language Processing," Frontiers in Psychology, vol. 3, Jun. 2012.
Pfaff, Mark S., "Negative Affect Reduces Team Awareness: The Effects of Mood and Stress on Computer-Mediated Team Communication," Human Factors, vol. 54, No. 4, Aug. 2012, pp. 560-571 DOI:10.1177/0018720811432307, Copyright © 2012, Human Factors and Ergonomics Society.
Paton, Douglas and Rhona Flin, "Disaster Stress: An Emergency Management Perspective," Disaster Prevention and Management, vol. 8, No. 4, 1999, pp. 261-267, MCB University Press, ISSN 0965-3562.
Fayemiwo, Michael A., et al. "Comparative Study and Detection of COVID-19 and Related Viral Pneumonia Using Fine-Tuned Deep Transfer Learning," Chhapter 2—Tracking and Preventing Diseases with Artificial Intelligence, Intelligent Systems Reference Library, vol. 206, ISSN 1868-4394, Jan. 2022.
Marco Pedrotti, Mohammad Ali Mirzaei, Adrien Tedesco, Jean-Remy Chardonnet, Frederic Merienne, Simone Benedetto, Thierry Baccino—Automatic Stress Classification With Pupil Diameter Analysis—International Journal of Human-Computer Interaction—vol. 30,n°3, p. 220-236—2014.
Nasir, Md, et at., "Modeling Vocal Entrainment in Conversational Speech Using Deep Unsupervised Learning," IEEE Transactions on Affective Computing, vol. 13, No. 3, Jul.-Sep. 2022.

* cited by examiner

| PHYSIOLOGICAL ACTIVITY (STRESS) | | VOCAL ENTRAINMENT |
|---|---|---|
| Alignment Orientation | Direction | Direction |
| Aligned | Decreasing | Positive |
| | | Negative |
| Not Aligned | Increasing Decreasing | Positive |
| | | Negative |
| Aligned | Increasing | Positive |
| | | Negative |

SYSTEM AND METHOD FOR REAL-TIME FEEDBACK OF REMOTE COLLABORATIVE COMMUNICATION

TECHNICAL FIELD

The present disclosure generally relates to collaborative communication, and more particular to a system and method for providing real-time feedback of remote collaborative communication.

BACKGROUND

There is presently a movement toward single pilot operations and urban air mobility (UAM). This movement is increasing the likelihood of remote teaming of individuals. For example, scalable autonomy procedures for UAM propose a ground supervisor collaborating remotely with multiple operators in the air. It is anticipated that, during certain operations, relatively high workload situations will be encountered. Although such situations will be mitigated as much as possible, it is likely that these remote teams will encounter stress.

Teams of two or more people that operate in high workload environments, in which the consequences of failure are heightened, are susceptible to stress and pressure. This stress and pressure can impact communication, collaboration, and team coordination. In addition, remote collaborations lack the communicative benefits of face-to-face interactions, meaning that individuals are missing the perceptual cues such as facial expressions and body language that can support understanding and communicative success, particularly during stressful situations.

A characteristic of successful teams is that the team members have entered a coordinative rhythm supportive of mutual understanding. This coordinative rhythm is measurable in speech. Sometimes called vocal entrainment, it occurs in a variety of complex patterns: speakers can mirror one another (synchrony), grow more similar over time (convergence), or match speaking patterns (proximity). The relationship between vocal entrainment and physiological stress has not yet been explored or utilized. This relationship may be significant in the context of high workload, high stress coordination of remote collaborators. Existing work has focused on the relationship between one individual's vocal features and their own physiological stress and how this can be used to detect a single individual's level of stress.

Hence, there is a need for a system and method to determine patterns of entrainment and stress that are indicative of social responses to support and manipulate collaboration, rapport, and stress responses in interactions between remote collaborators.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one embodiment, a system for providing real-time feedback of remote collaborative communication between a first user and a second user includes a processing system that is configured to: extract a plurality of first speech-related features from first audio signals generated in response to speech supplied from the first user; extract a plurality of first physiological features from the first audio signals, first physiological data generated in response to physiological activity of the first user, or both; extract a plurality of second speech-related features from second audio signals generated response to speech supplied from the second user; extract a plurality of second physiological features from the second audio signals, second physiological data generated in response to physiological activity of the second user, or both; process the first and second speech-related features to determine if the speech from the first and second users exhibits positive or negative vocal entrainment; process the first and second physiological features to determine if physiological states of the first and second users are aligned or misaligned; and generate commands that cause at least one device to supply feedback that indicates (i) if the speech from the first and second users exhibits positive or negative vocal entrainment and (ii) if the physiological activity of the first and second users is aligned or misaligned.

In another embodiment, a method for providing real-time feedback of remote collaborative communication includes processing first audio signals to extract a plurality of first speech-related features therefrom, the first audio signals being supplied in response to speech supplied from a first user; processing the first audio signals, first physiological data, or both, to extract a plurality of first physiological activity features therefrom, the first physiological data being supplied in response to physiological activity of the first user; processing second audio signals to extract a plurality of second speech-related features therefrom, the second audio signals being supplied in response to speech supplied from a second user; processing the second audio signals, second physiological activity data, or both, to extract a plurality of second physiological features therefrom, the second physiological activity data being supplied in response to physiological activity of the second user; processing the first and second speech-related features to determine if the speech from the first and second users exhibits positive or negative vocal entrainment; processing the first and second physiological features to determine if physiological states of the first and second users are aligned or misaligned; and generating feedback, via at least one human-machine interface, that indicates (i) if the speech from the first and second users exhibits positive or negative vocal entrainment and (ii) if the physiological states of the first and second users are aligned or misaligned.

In yet another embodiment, a system for providing real-time feedback of remote collaborative communication between a first user and a second user includes a processing system that is configured to: extract a plurality of first speech-related features from first audio signals generated in response to speech supplied from the first user; extract a plurality of physiological features from the audio signals, first physiological data generated in response to physiological activity of the first user, or both; process the first speech-related features and the first physiological activity features to determine a stress state of the first user; and in response to the determined stress state of the first user: (i) automatically process second audio signals generated in response to speech supplied from the second user to manipulate one or more vocal features of the speech supplied from the second user; and/or (ii) generate commands that cause at least one device to supply feedback to the second user that provide suggestions to the second user as to how to manipulate or more of their vocal features.

Furthermore, other desirable features and characteristics of the system and method for providing real-time feedback of remote collaborative communication will become apparent from the subsequent detailed description and the appended claims, taken in conjunction with the accompanying drawings and the preceding background.

BRIEF DESCRIPTION OF DRAWINGS

The present disclosure will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
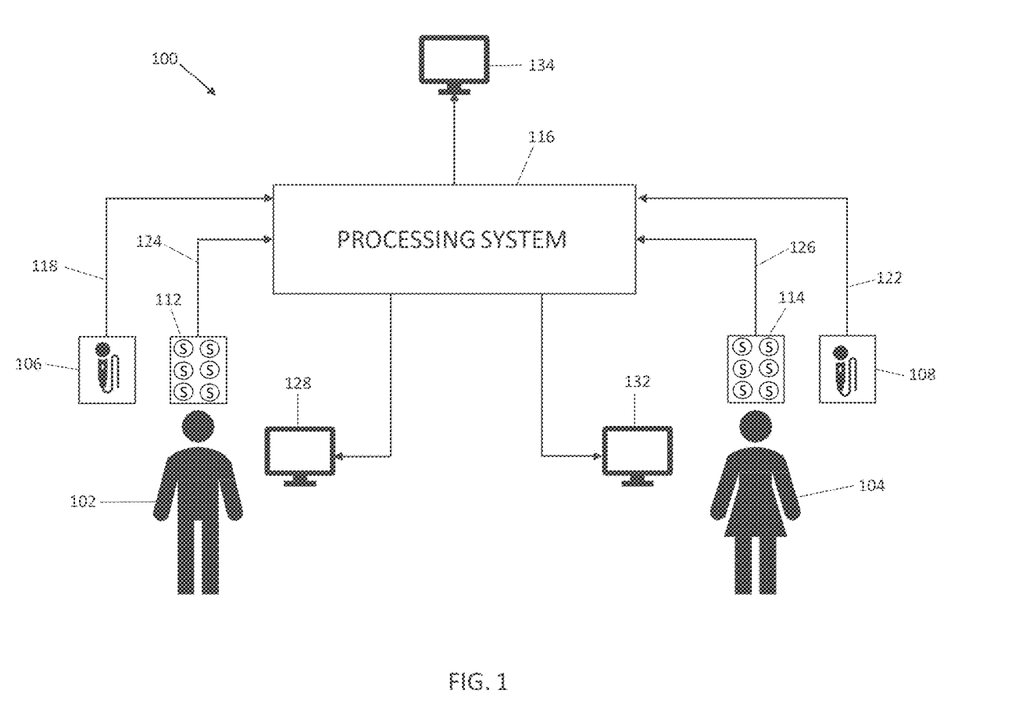
FIG. 1 depicts a functional block diagram of one embodiment of a system for providing real-time feedback of remote collaborative communication between a plurality of users.

Referring now to FIG. 1, a functional block diagram of a system 100 for providing real-time feedback of remote collaborative communication between a plurality of users is depicted. It should be noted that, for ease of depiction and description, only two users—a first user 102 and a second user 104—are depicted in FIG. 1. It will be appreciated, however, that the system 100 can be used for remote collaboration between more than two users.

The depicted system 100, in which only two users 102, 104 are included, includes at least a first microphone 106, a second microphone 108, and a processing system 116. As FIG. 1 also depicts, the system 100 may also, in some embodiments, include a plurality of first physiological sensors 112, a plurality of second physiological sensors 114, The first microphone 106 is configured to receive speech supplied from the first user 102 and is operable, in response thereto, to supply first audio signals 118. The second microphone 108 is configured to receive speech supplied from the second user 104 and is operable, in response thereto, to supply second audio signals 122. It will be appreciated that the first and second microphones 106, 108 may be implemented using any one of numerous devices, now known or developed in the future, that convert vocal induced pressure variations to electrical signals. Some non-limiting examples include any one of numerous dynamic microphones, condenser microphones, and contact microphones, just to name a few.

When included, the first physiological sensors 112 are disposed on the first user 102 and are configured to supply the first physiological data 124 to the processing system 116. The second physiological sensors 114, when included, are disposed on the second user 104 and are configured to supply the second physiological data 126 to the processing system 116. It will be appreciated that the first and second physiological sensors 112, 114 may be implemented using any one of numerous devices, now known or developed in the future, that sense and supply physiological data. Some non-limiting examples include electrocardiogram (EKG) sensors, oxygen saturation (SpO2) sensors, galvanic skin response sensors, breath-rate sensors, pupil diameter sensors, and vocal and linguistic sensors.

The processing system 116 may include one or more processors and computer-readable storage devices or media encoded with programming instructions for configuring the processing system 116. The one or more processors may be any custom-made or commercially available processor, a central processing unit (CPU), a graphics processing unit (GPU), an application specific integrated circuit (ASIC), a field programmable gate array (FPGA), an auxiliary processor among several processors associated with the controller, a semiconductor-based microprocessor (in the form of a microchip or chip set), any combination thereof, or generally any device for executing instructions.

The computer readable storage devices or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable programming instructions, used by the controller.

The processing system 116 is coupled to receive the first and second audio signals 118, 122 and, in some embodiments, may additionally receive the first and second physiological data 124, 126. The processing system 116 is configured to extract a plurality of first speech-related features from the first audio signals, and a plurality of second speech-related features from the second audio signals. The processing system 116 is configured to process the first and second speech-related features to determine if the speech from the first and second users 102, 104 exhibits positive or negative vocal entrainment.

Before proceeding further, it is noted that vocal entrainment is a known temporal phenomenon that has been shown to be one of several critical factors that impacts conversational success, including task success, rapport, and trust. Vocal entrainment can be positive, where the speakers are aligning and adapting to one another to become more similar over the course of a conversation, or it can be negative, where the opposite is occurring.

Returning now to the description, to assess vocal entrainment, the first and second audio signals 118, 122 are transformed to allow for the speech-related feature extraction. The first and second speech-related features that the processing system 116 is configured to extract include, but are not limited to, extraction of pitch, speaking rate, intensity, jitter (pitch period length deviations), and shimmer (amplitude deviations between pitch period lengths). The processing system 116 may implement any one of numerous known techniques to extract the speech-related features. For example, the processing system 116 may use PRAAT or openSMILE, both of which are known computer programs for analyzing, synthesizing, and manipulating speech. PRAAT is disclosed, for example, in "PRAAT, a system for doing phonetics by computer," authored by P. Boersma, and published in Glot Int., vol. 5, 2002, and openSMILE is disclosed, for example, in "openSMILE—The Munich Versatile and Fast Open-Source Audio Feature Extractor Categories and Subject Descriptors," authored by F. Eyben, M. Wöllmer, and B. Schuller, and published in Proceedings of the 18th ACM international conference on Multimedia, 2010, pp. 1459-1462. Both of these publications are incorporated herein by reference in their entirety.

Figure 2:
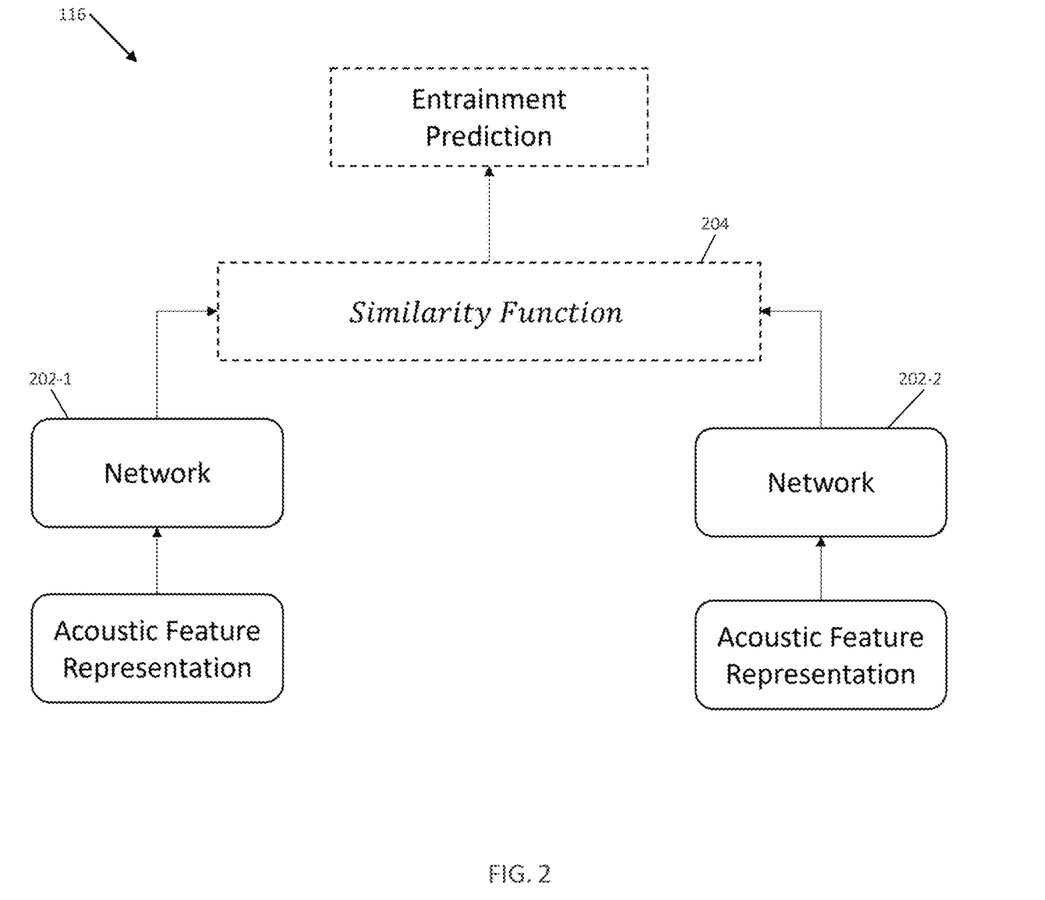
FIG. 2 depicts one embodiment of a processing system implementing a Siamese Neural Network approach.

The processing system 116 may also implement any one of numerous known techniques to determine if the speech from the first and second users 102, 104 exhibits positive or negative vocal entrainment. For example, the processing system 116 may implement a deep-learning approach using an unsupervised deep learning framework as disclosed in "Towards an Unsupervised Entrainment Distance in Conversational Speech using Deep Neural Networks," authored by M. Nasir, B. Baucom, S. Narayanan, and P. Georgiou, published in arXiv, 2018. In one particular embodiment, the processing system 116 implements a Siamese Neural Network approach, as illustrated in FIG. 2. This approach involves training two neural networks 202 (202-1, 202-2) to learn a similarity function 204. In a preferred embodiment, the two neural networks 202 are trained to learn patterns of acoustic similarity between two utterances of conversational speakers (e.g., first and second users 102, 104).

The processing system 116 may also be configured, in some embodiments, to extract a plurality of first physiological features from the first physiological data 124, and to extract a plurality of second physiological features from the second physiological data 126. The processing system 116, in these embodiments, also processes the first and second physiological features to determine if the physiological states of the first and second users 102, 104 are aligned or misaligned. More specifically, at least in one embodiment, the processing system 116 is configured to correlate the first and second physiological features to a stress state of the first and second user, respectively.

It will be appreciated that in other embodiments, in which the system 100 does not include the first and second physiological sensors 124, 126, the processing system 116 is configured to extract the first and second physiological features from the first and second audio signals, respectively. In still other embodiments, the processing system 116 is configured to extract the first and second physiological features from both the first and second audio signals and the first and second physiological data to a stress state of the first and second user, respectively.

It will be appreciated that the processing system 116 may implement any one of numerous known techniques to correlate the physiological features to a stress state. For example, the processing system 116 may use pupil diameter to automatically classify stress with a neural networks, as disclosed in "Automatic Stress Classification With Pupil Diameter Analysis," authored by M. Pedrotti, M. Mirzaei, A. Tedesco, J. Chardonnet, F. Mérienne, S. Benedetto, and T. Baccino, published in the International Journal of Human-Computer Interaction, vol. 30, no. 3, 2014, pp. 220-236, or speech to classify stress and emotion with discriminant analysis, as disclosed in "Stress Identification from Speech Using Clustering Techniques," authored by B. Prasetio, H. Tamura, and K. Tanno, published in 2020 Joint 9th International Conference on Informatics, Electronics & Vision (ICIEV) and 2020 4th International Conference on Imaging, Vision & Pattern Recognition (icIVPR), 2020, just to name two non-limiting examples.

Regardless of the specific techniques used to extract the speech-related features and the physiological features, the processing system 116 is additionally configured to process the first and second speech-related features to determine if the speech from the first and second users 102, 104 exhibits positive or negative vocal entrainment, and to process the first and second physiological features to determine if the physiological states (e.g., stress states) of the first and second users 102, 104 are aligned or misaligned and to determine if the physiological states (e.g., stress states) of the first and second users 102, 104 are increasing or decreasing. The processing system 116 may implement various known techniques to make these determinations. For example, the processing system 116 may determine if the speech from the first and second users exhibits positive or negative vocal entrainment by evaluating turn-by-turn feature similarity and increasing or decreasing alignment in terms of change over time across multiple speech features. Likewise, the processing system 116 may determine if the physiological states of the first and second users are aligned or misaligned and increasing or decreasing by comparing the physiological features via autocorrelation, analysis of short sequences, and comparison to established patterns.

Figure 3:
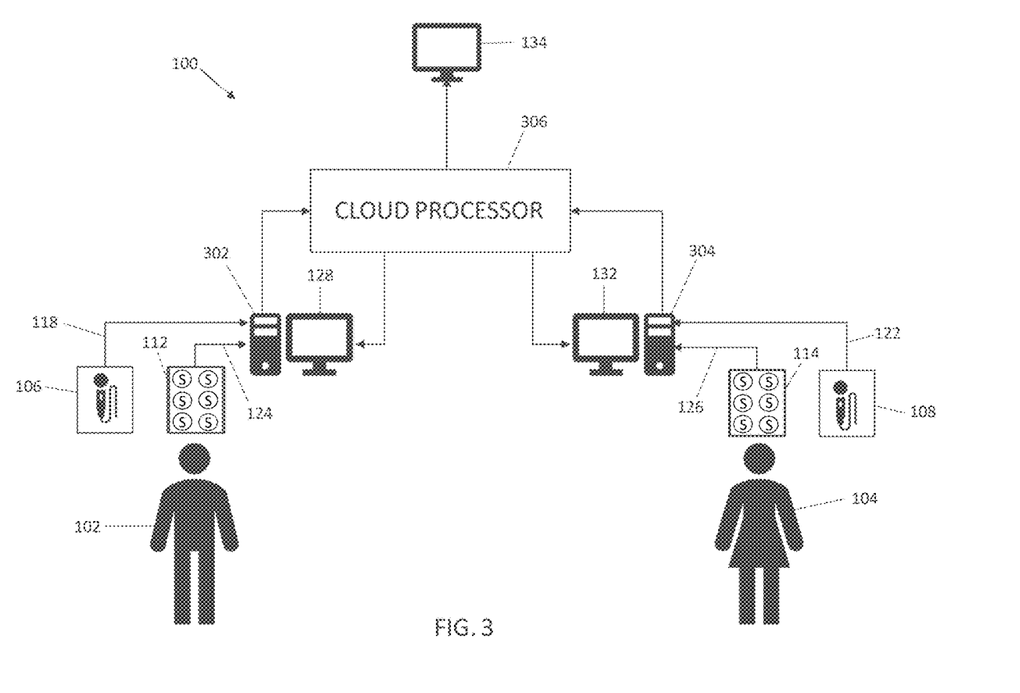
FIG. 3 depicts a functional block diagram of another embodiment of a system for providing real-time feedback of remote collaborative communication between a plurality of users.

Before proceeding further, it was previously noted that the processing system 116 may include one or more processors. Indeed, as FIG. 3 depicts, in one embodiment, the processing system 116 is implemented using at least three separate processors—a first local processor 302, a second local processor 304, and a cloud processor 306. The first local processor 302 is collocated with the first user 102 and is coupled to receive and process the first audio signals and the first physiological data and to transmit the first speech-related features and the first physiological features to the cloud processor 306. The second local processor 304 is collocated with the second user 104 and is coupled to receive and process the second audio signals and the second physiological data and to transmit the second speech-related features and the second physiological features to the cloud processor 306. The cloud processor 306 is configured to receive and process the first and second speech-related features to determine if the speech from the first and second users exhibits positive or negative vocal entrainment. The cloud processor 306 is additionally configured to receive and process the first and second physiological features to determine if the physiological states of the first and second users are aligned or misaligned and increasing or decreasing. Thus, the audio signal and physiological data processing is implemented locally by the first and second local processors 302, 304, thereby reducing potential data loss. However, the vocal entrainment and physiological state alignment and analysis occurs centrally at the cloud processor 306.

Figure 4:
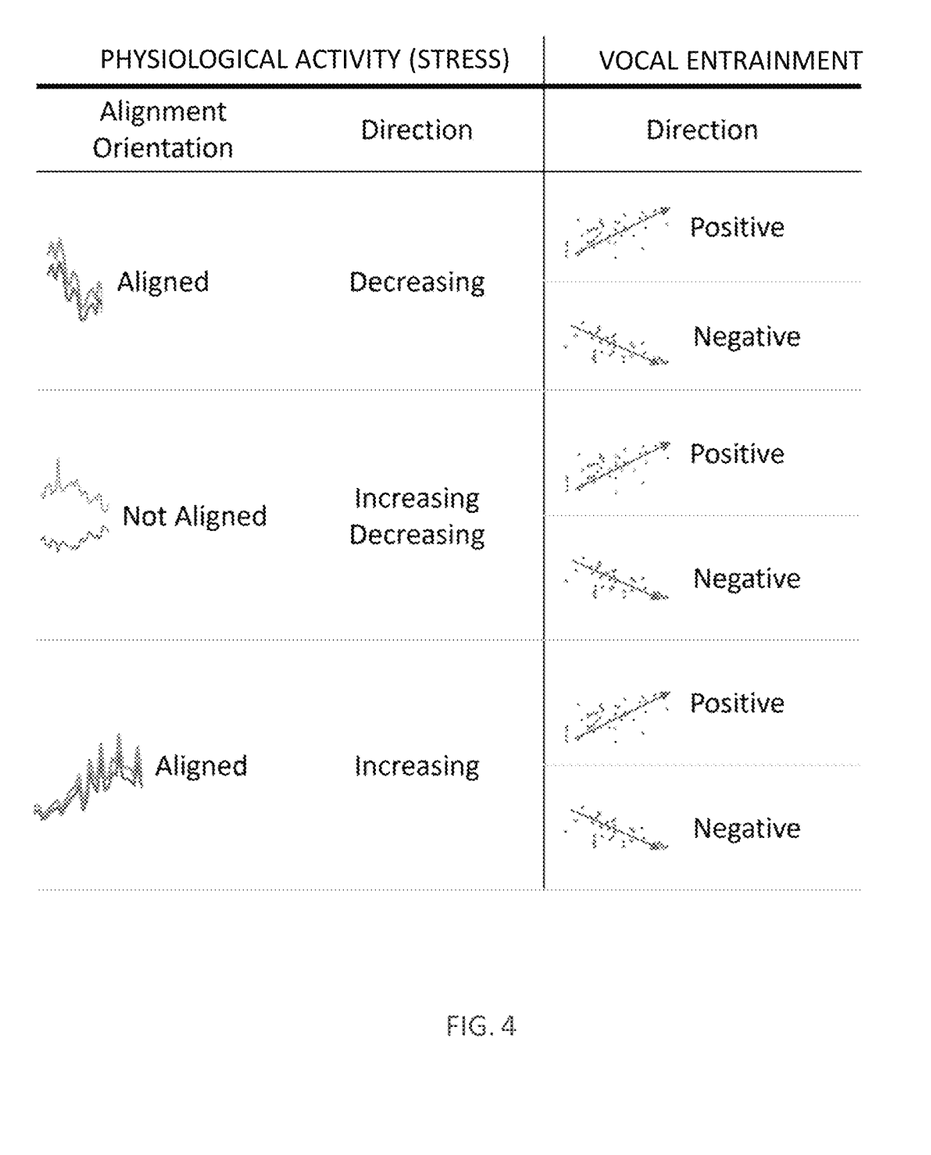
FIG. 4 depicts the type of feedback that the system depicted in FIGS. 1 and 3 can provide to a plurality of users.

Regardless of the number of processors that are used to implement the processing system 116, and as FIG. 4 depicts, the vocal entrainment and physiological state alignment and analysis can be depicted as falling into one of six different combinations that provide indicative information regarding communicative interactions. A first combination is when the physiological states of the first and second users 102, 104 are aligned and decreasing, and the first and second users 102, 104 exhibit positive vocal entrainment. A second combination is when the physiological states of the first and second users 102, 104 are aligned and decreasing, and the first and second users 102, 104 exhibit negative vocal entrainment. A third combination is when the physiological states of the first and second users 102, 104 are misaligned (and either or both are increasing or decreasing), and the first and second users 102, 104 exhibit positive vocal entrainment. A fourth combination is when the physiological states of the first and second users 102, 104 are misaligned (and either or both are increasing or decreasing), and the first and second users 102, 104 exhibit negative vocal entrainment. A fifth combination is when the physiological states of the first and second users 102, 104 are aligned and increasing, and the first and second users 102, 104 exhibit positive vocal entrainment. A sixth combination is when the physiological states of the first and second users 102, 104 are aligned and increasing, and the first and second users 102, 104 exhibit negative vocal entrainment.

The information depicted in FIG. 4 may be provided as real-time feedback of the remote collaborative communication. To do so, the processing system 116 is additionally configured to generate commands that cause at least one human-machine interface to render feedback. This feedback, which may correlate to the individual combinations depicted in FIG. 4, indicates if the speech from the first and second users 102, 104 exhibits positive or negative vocal entrainment and if the physiological states of the first and second users 102, 104 is aligned or misaligned and if the physiological states of the first and second users is increasing or decreasing. In a particular preferred embodiment, the system 100 includes a human-machine interface associated with each user. Thus, as FIGS. 1 and 3 depict, the system 100 further includes a first user human-machine interface 128 and a second user human-machine interface 132. The first user human-machine interface 128 is collocated with the first user 102, and the second user human-machine interface 132 is collocated with the second user 104. The first and second human-machine interfaces 128, 132 are both coupled to receive the commands from the processing system 116, and to supply the appropriate feedback.

It will be appreciated that the real-time feedback provided to one or both users 102, 104 is not limited to positive/negative vocal entrainment and/or physiological state alignment/misalignment and trends. Indeed, the feedback provided to the first and second users 102, 104 preferably takes into account not only the physiological states of the first and second users 102, 104, but also the environment, and task context. This feedback may include several embodiments or combinations of embodiments. Some examples of such feedback include, but are not limited to, providing explicit recommendations about how the first and second users 102, 104 can change their approach to the task, their linguistic or para-linguistic (e.g., tone, speaking pace) features, or the environment to achieve better collaborative success. The feedback may also (or instead) contain implicit recommendations about how to interact with the other user or it may simply convey information indicating that there is a positive or negative collaboration.

In another embodiment, as FIGS. 1 and 2 also depict, the system 100 may include a third human-machine interface 134. This third human-machine interface 134, when included, is disposed remote from the first and second user human-machine interfaces 128, 132, and is also coupled to receive the commands from the processing system 116. The third human-machine interface 134, when included, may be used by a third user (not depicted) or third party (not depicted) for training and/or debriefing purposes.

It will be appreciated that the first, second, and third human-machine interfaces 128, 132, 134 may be implemented using any one of numerous types of human-machine interfaces. For example, one or more may be implemented using a display device to render images, or using a sound emitter to supply auditory feedback, a hand-held computing device to render images and/or supply auditory feedback, or various combinations of these devices, just to name a few.

Figure 5:
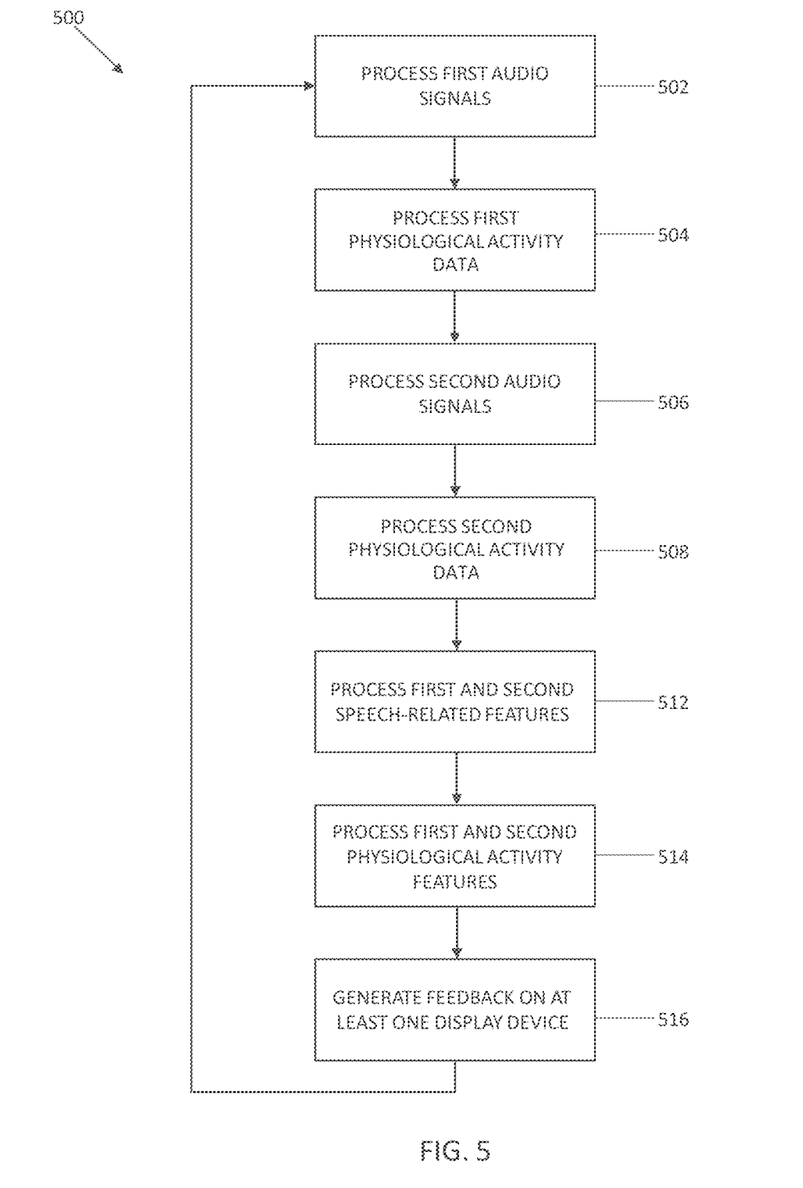
FIG. 5 depicts a process flowchart of an example process for providing real-time feedback of remote collaborative communication using the systems of FIG. 1 or 3.

Referring now to FIG. 5, a process flowchart is depicted of one example process 500 for providing real-time feedback of remote collaborative communication. The order of operation within the process 500 is not limited to the sequential execution as illustrated in the figure, but may be performed in one or more varying orders as applicable and in accordance with the present disclosure. Moreover, as will be explained further below, some of the depicted steps may not be performed at all.

The example process 500 includes processing first audio signals to extract a plurality of first speech-related features (502), and processing the first audio signals, first physiological data, or both, to extract a plurality of first physiological features (504). The example process 500 also includes processing second audio signals to extract a plurality of second speech-related features (506), and processing the second audio signals, second physiological data, or both, to extract a plurality of second physiological features (508).

The example process 500 includes processing the first and second speech-related features to determine if the speech from the first and second users exhibits positive or negative vocal entrainment (512), and processing the first and second physiological features to determine if the physiological states of the first and second users are aligned or misaligned (514).

The example process 500 includes generating feedback via at least one human-machine interface (516). As noted above, this feedback indicates if the speech from the first and second users exhibits positive or negative vocal entrainment and if the physiological states of the first and second users are aligned or misaligned, and whether the states are increasing or decreasing.

The systems and methods described thus far is in the context of remote communications where physiological data indicative of a stress response and vocal signal information indicative of entrainment is collected from all of the users as they communicate. However, in some embodiments, such as the one depicted in FIG. 6, information is obtained from only one user. This system 600, in which only two users 102, 104 are included, includes a first microphone 606, a second microphone 608, and a processing system 616, and may additionally include a plurality of first physiological sensors 612. The first microphone 606 is configured to receive speech supplied from the first user 102 and is operable, in response thereto, to supply first audio signals 618. The second microphone 608 is configured to receive speech supplied from the second user 104 and is operable, in response thereto, to supply second audio signals 622. It will be appreciated that the first microphone 606 may be implemented using any one of numerous devices, now known or developed in the future, that convert vocal induced pressure variations to electrical signals. Some non-limiting examples include any one of numerous dynamic microphones, condenser microphones, and contact microphones, just to name a few.

Figure 6:
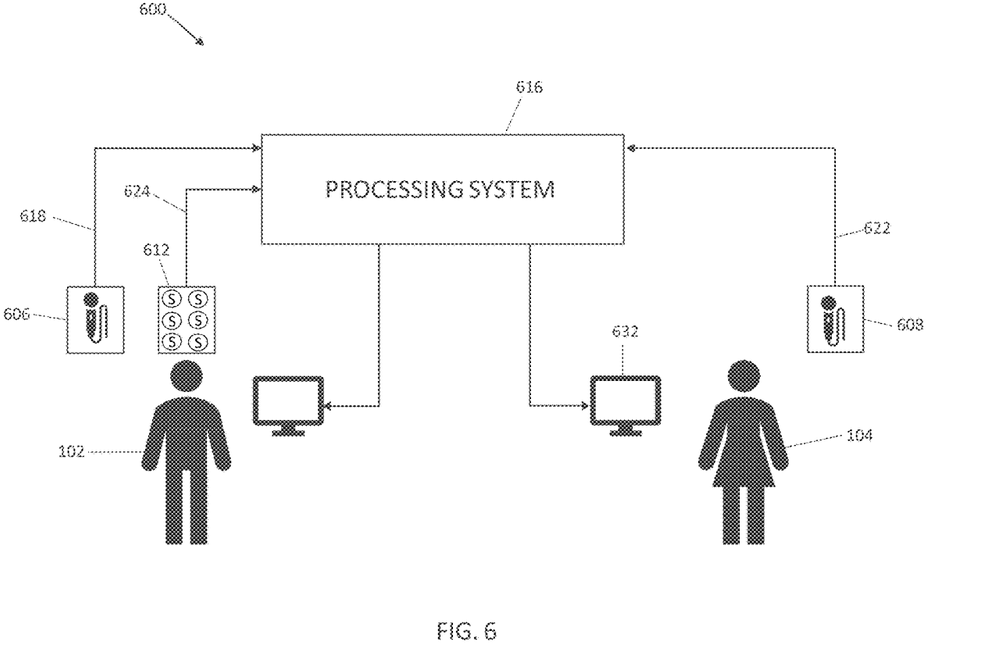
FIG. 6 depicts a functional block diagram of yet another embodiment of a system for providing real-time feedback of remote collaborative communication between a plurality of users.

The first physiological sensors 612, when included, are disposed on the first user 102 and are configured to supply first physiological data 624 to the processing system 116. It will be appreciated that the first physiological sensor 612 may be implemented using any one of numerous devices, now known or developed in the future, that sense and supply physiological data. Some non-limiting examples include electrocardiogram (EKG) sensors, oxygen saturation (SpO2) sensors, galvanic skin response sensors, breath-rate sensors, pupil diameter sensors, and vocal and linguistic sensors.

The processing system 616 may include one or more processors and computer-readable storage devices or media encoded with programming instructions for configuring the processing system 616. The one or more processors may be any custom-made or commercially available processor, a central processing unit (CPU), a graphics processing unit (GPU), an application specific integrated circuit (ASIC), a field programmable gate array (FPGA), an auxiliary processor among several processors associated with the controller, a semiconductor-based microprocessor (in the form of a microchip or chip set), any combination thereof, or generally any device for executing instructions.

The computer readable storage devices or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable programming instructions, used by the controller.

The processing system 616 is coupled to receive the first audio signals 618 and, when the first physiological sensors 612 are included, the first physiological data 624. The processing system 616 is configured to extract a plurality of first speech-related features from the first audio signals 618, and extract a plurality of physiological features from the first physiological data 624, when the first physiological sensors 612 are included, or from the first audio signals 618, or both. The processing system 616 is additionally configured to process only the first speech-related features, or the first speech-related features and the first physiological features, to determine a stress state of the first user 102. It will be appreciated that the processing system 616 may implement any one of the previously mentioned known techniques to correlate the speech-related features and/or the physiological features to a stress state.

The processing system 616 is further configured, based on the determined stress state of the first user 102, to selectively (and automatically) process the second audio signals 622 to manipulate one or more vocal features (e.g., pitch, intensity, speech-rate) of the speech supplied from the second user 104. The processing system 616 may additionally, or instead, generate commands that cause a human-machine interface 632 to supply feedback to the second user 104 that provide suggestions to the second user 104 as to how to manipulate one or more of their vocal features. The human-machine interface 632, when included, is collocated with the second user 104, is coupled to receive commands from the processing system 116, and to supply the appropriate suggestions.

Figure 7:
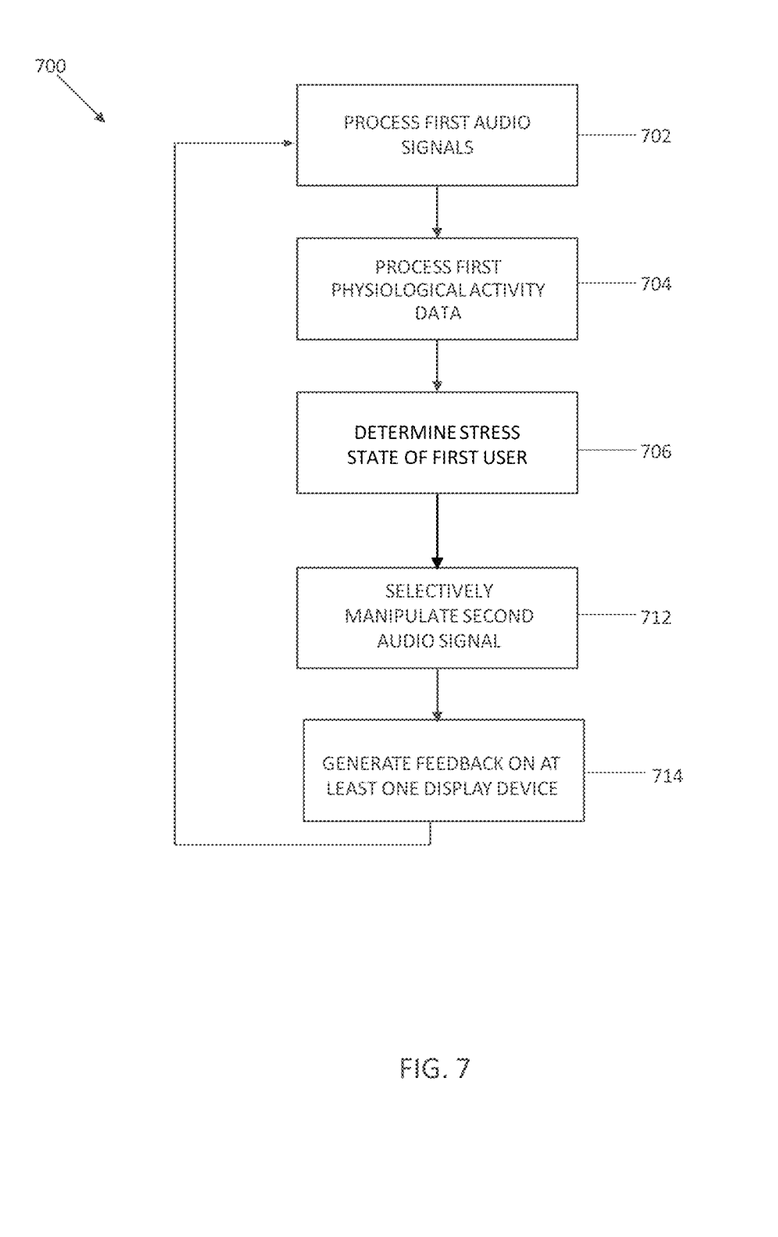
FIG. 7 depicts a process flowchart of an example process for providing real-time feedback of remote collaborative communication using the system of FIG. 6.

Referring now to FIG. 7, a process flowchart is depicted of an example process 400 for providing real-time feedback of remote collaborative communication. The order of operation within the process 700 is not limited to the sequential execution as illustrated in the figure, but may be performed in one or more varying orders as applicable and in accordance with the present disclosure.

The example process 700 includes processing first audio signals to extract a plurality of first speech-related features (702), and processing first physiological data to extract a plurality of first physiological features (704). The example process 700 further includes processing the first speech-related features and the first physiological features to determine a stress state of the first user 102 (706). Based on the determined stress state of the first user 102, one or more vocal features (e.g., pitch, intensity, speech-rate) of the second audio signals 622 may be automatically manipulated (712). The example process 700 may also (or instead) include generating feedback via at least one human-machine interface (714). As noted above, this feedback provide suggestions to the second user 104 as to how to manipulate one or more of their vocal features.

The systems and methods disclosed herein determine patterns of entrainment and stress that are indicative of social responses to support and manipulate collaboration, rapport, and stress responses in interactions between remote collaborators.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium", "processor-readable medium", or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system for providing real-time feedback of remote collaborative communication between a first user and a second user, the system comprising:
   a non-transitory computer-readable medium storing instructions; and
   a processing system, including at least one specialized processor, that is configured to execute the stored instructions to:
   extract a plurality of first speech-related features from first audio signals generated in response to speech supplied from the first user;
   extract a plurality of first physiological features from the first audio signals, first physiological data generated in response to physiological activity of the first user, or both, wherein the first physiological data is obtained from one or more first physiological sensors;
   extract a plurality of second speech-related features from second audio signals generated response to speech supplied from the second user;
   extract a plurality of second physiological features from the second audio signals, second physiological data generated in response to physiological activity of the second user, or both, wherein the second physiological data is obtained from one or more second physiological sensors;
   process the first and second speech-related features to determine if the speech from the first and second users exhibits positive or negative vocal entrainment;
   process the first and second physiological features to determine if physiological states of the first and second users are aligned or misaligned; and
   generate commands that cause at least one device to supply real-time, adaptive multimodal feedback that indicates:
      (i) whether the speech from the first and second users exhibits positive or negative vocal entrainment, and
      (ii) whether the physiological activity of the first and second users is aligned or misaligned.

2. The system of claim 1, wherein the processing system is further configured to:
   process the first and second physiological features to determine if the physiological states of the first and second users are increasing or decreasing; and
   generate commands that cause the at least one device to supply feedback that indicates if the physiological states of the first and second users are increasing or decreasing.

3. The system of claim 1, further comprising:
   a first microphone configured to receive the speech supplied from the first user and, in response thereto, supply the first audio signals to the processing system; and
   a second microphone configured to receive the speech supplied from the second user and, in response thereto, supply the second audio signals to the processing system.

4. The system of claim 1, further comprising:
   the plurality of first physiological sensors disposed on the first user and configured to supply the first physiological data to the processing system; and
   the plurality of second physiological sensors disposed on the second user and configured to supply the second physiological data to the processing system.

5. The system of claim 1, further comprising:
   a first human-machine interface coupled to receive the commands from the processing system; and
   a second user human-machine interface coupled to receive the commands from the processing system.

6. The system of claim 5, further comprising:
   a third human-machine interface disposed remote from the first and second human-machine interfaces, the third human-machine interface coupled to receive the commands from the processing system.

7. The system of claim 1, wherein the first and second speech-related features that the processing system is configured to extract comprise: pitch, speech rate, intensity, jitter, and shimmer.

8. The system of claim 1, wherein the first and second physiological features that the processing system is configured to extract comprise one or more of: heart rate, breath rate, oxygen saturation level, pupil diameter, and galvanic skin response.

9. The system of claim 1, wherein the processing system is configured to correlate the physiological state of the first and second users to a stress state of the first and second user, respectively, and determine if the stress state of the first and second users is aligned or misaligned.

10. The system of claim 1, wherein the processing system comprises:
    a first local processor coupled to receive and process the first audio signals and the first physiological data and to transmit the first speech-related features and the first physiological features;
    a second local processor coupled to receive and process the second audio signals and the second physiological data and to transmit the second speech-related features and the second physiological features; and
    a cloud processor coupled to receive and process (i) the first and second speech-related features to determine if the speech from the first and second users exhibits positive or negative vocal entrainment and (ii) the first and second physiological features to determine if the physiological states of the first and second users are aligned or misaligned.

* * * * *